(12) United States Patent
Drewes, Jr. et al.

(10) Patent No.: US 11,534,532 B2
(45) Date of Patent: Dec. 27, 2022

(54) HYDROPHOBICALLY ENCASED TUNGSTEN

(71) Applicant: Cook Medical Technologies LLC, Bloomington, IN (US)

(72) Inventors: David A. Drewes, Jr., Bloomington, IN (US); Brian Tankersley, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 282 days.

(21) Appl. No.: 15/897,299

(22) Filed: Feb. 15, 2018

(65) Prior Publication Data
US 2018/0236140 A1  Aug. 23, 2018

Related U.S. Application Data

(60) Provisional application No. 62/461,917, filed on Feb. 22, 2017.

(51) Int. Cl.
| | | |
|---|---|---|
| *A61L 29/18* | (2006.01) | |
| *A61M 25/01* | (2006.01) | |
| *A61L 29/04* | (2006.01) | |
| *A61L 29/14* | (2006.01) | |
| *A61L 29/08* | (2006.01) | |
| *A61L 29/12* | (2006.01) | |

(52) U.S. Cl.
CPC ............ *A61L 29/18* (2013.01); *A61L 29/041* (2013.01); *A61L 29/085* (2013.01); *A61L 29/126* (2013.01); *A61L 29/14* (2013.01); *A61M 25/0108* (2013.01); *A61L 2400/12* (2013.01)

(58) Field of Classification Search
CPC .......... A61L 29/14; A61L 29/18; A61L 31/18; A61M 25/0108
See application file for complete search history.

(56) References Cited

U.S. PATENT DOCUMENTS

| | | | |
|---|---|---|---|
| 5,300,048 A | 4/1994 | Drewes, Jr. et al. | |
| 6,077,880 A | 6/2000 | Castillo et al. | |
| 6,331,329 B1 | 12/2001 | McCarthy et al. | |
| 6,355,058 B1 | 3/2002 | Pacetti et al. | |
| 7,483,732 B2 * | 1/2009 | Zhong ................. | G01R 33/285 |
| | | | 324/309 |
| 2004/0073158 A1 | 4/2004 | Shah et al. | |
| 2005/0064223 A1 | 3/2005 | Bavaro et al. | |

(Continued)

FOREIGN PATENT DOCUMENTS

| | | |
|---|---|---|
| JP | 2007-505721 | 3/2007 |
| WO | WO 2005/030284 A2 | 4/2005 |

OTHER PUBLICATIONS

Communication According to Article 94(3) for EP 18 155 115.1, dated Aug. 23, 2019, 5 pp.

(Continued)

*Primary Examiner* — Nathan R Price
*Assistant Examiner* — Anh Bui
(74) *Attorney, Agent, or Firm* — Crowell & Moring LLP

(57) ABSTRACT

Disclosed herein are compositions of matter for inclusion in a medical device for visualization purposes. Such compositions may include a radiopaque metal, such as tungsten, within a functionalized hydrophobic polymer. Methods of making devices incorporating such elements are also disclosed.

19 Claims, 2 Drawing Sheets

(56) References Cited

U.S. PATENT DOCUMENTS

| | | | | |
|---|---|---|---|---|
| 2005/0065434 A1* | 3/2005 | Bavaro | ............... | A61L 29/18 |
| | | | | 600/424 |
| 2009/0036768 A1* | 2/2009 | Seehusen | ............ | A61L 29/106 |
| | | | | 600/424 |
| 2010/0130962 A1* | 5/2010 | Ebert | ............. | A61M 25/0108 |
| | | | | 604/529 |
| 2010/0130963 A1 | 5/2010 | Ebert et al. | | |
| 2015/0283301 A1 | 10/2015 | Semetey et al. | | |

OTHER PUBLICATIONS

Extended European Search Report for EP 18 155 115.1, dated Jul. 13, 2018, 7 pp.
Search Report and Opinion for EP 18 155 115, dated Jul. 5, 2018, 5 pp.
Notification of First Office Action for corresponding Chinese patent application No. 201810153606.7, dated Jun. 17, 2021, 9 pgs.
English Translation of First Office Action for corresponding Chinese patent application No. 201810153606.7, dated Jun. 17, 2021, 5 pgs.
Office Action in Corresponding Japanese Patent Application No. 2018-028735 dated Sep. 28, 2021, 5 pages.

* cited by examiner

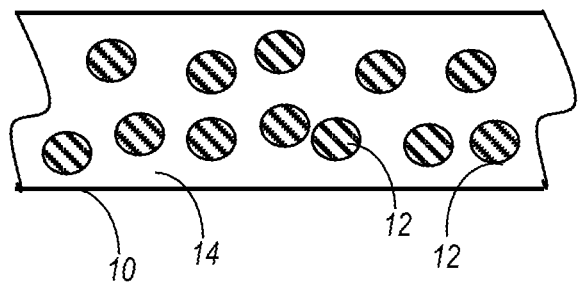
FIG. 1
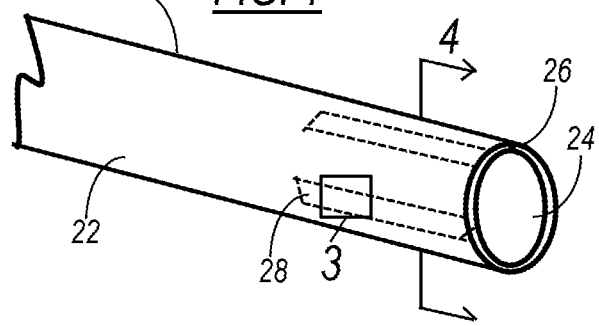
FIG. 2
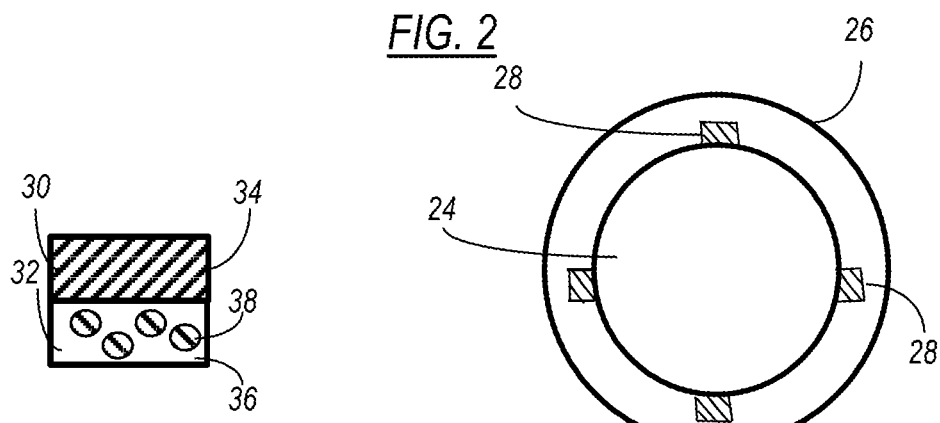
FIG. 3
FIG. 4
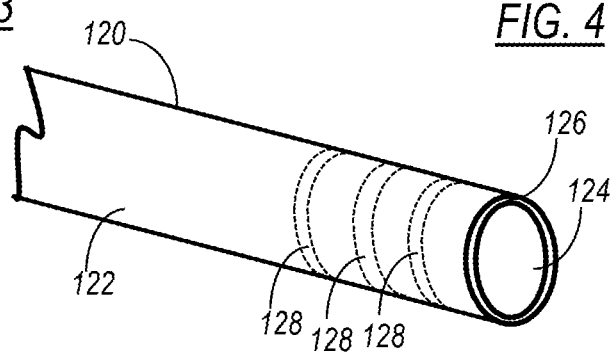
FIG. 5

HYDROPHOBICALLY ENCASED TUNGSTEN

CROSS-REFERENCE TO RELATED APPLICATIONS

This application claims priority from U.S. Provisional Application Ser. No. 62/461,917, filed on Feb. 22, 2017, the entirety of which is hereby incorporated herein by reference.

BACKGROUND

The present application generally relates to medical devices. More particularly, the present application relates to devices for use within a body lumen, including catheters, which are made principally of a polymeric material and incorporate a radiopaque element.

Medical insertion and delivery procedures may be monitored by fluoroscopy, angiograms, CT scanning, radiography, or the like. Radiopaque markers are commonly used as landmarks on components of the delivery system, including but not limited to a wire guide, a catheter and a medical implant to be delivered. Monitoring assists in assuring accurate positioning of the device at the site of implantation and its full deployment.

Radiopaque elements or markers are incorporated into the devices at the time of manufacture. Typically, a metal capable of reflecting X-rays is introduced into the portion of the device which is to be followed, for example the struts of an intravascular filter. In some cases, the process of incorporating the metal into the structure is straightforward, for example when a small portion of a metallic device is constructed of a radiopaque metal. In other cases, such as when a device is made of plastic, the metal is mixed with a material having similar chemical characteristics to the remainder of the device. For example, a metal component may be provided with a silicone coating and then incorporated into a silicone instrument.

One type of metal which has been used as a radiopaque element is tungsten. Tungsten is a dense metal, which provides reliable signal during monitoring. It is also cost-effective to use tungsten, at a typical cost of less than about $25 per kilogram. However, the presence of tungsten may promote degradation of a polymer in which it is encased. This may lead to breakdown under hospital sterilization conditions, which can involve high humidity and heat. This may also lead to a relatively shortened shelf life of packaged devices.

It has been a challenge to develop a radiopaque element for a medical device which can withstand adverse environmental conditions and which have improved shelf life.

SUMMARY

In one aspect, the present disclosure provides a medical device which includes a body portion comprising a first polymeric material, and a visualization portion comprising a second polymeric material more hydrophobic than the first polymeric material. The visualization portion may include a plurality of particles comprising at least one radiopaque metal. At least some of the plurality of particles are in direct contact with and combined, compounded, or dispersed in the second polymeric material. The second polymeric material may be in direct contact with the first polymeric material.

In another aspect, the present disclosure provides a method of making a medical device. The method includes dispersing a radiopaque material into a functionalized hydrophobic polymer to form a visualization element. The radiopaque material may be in direct contact with the functionalized hydrophobic polymer. The method also includes bonding the visualization element to a device body of the medical device.

Further objects, features and advantages of this system will become readily apparent to persons skilled in the art after a review of the following description, with reference to the drawings and claims that are appended to and form a part of this specification.

BRIEF DESCRIPTION OF THE DRAWINGS

FIG. 1 is a schematic depiction of metal particles compounded into a polymer substrate in accordance with one embodiment of the present invention;

FIG. 2 is a perspective view of the distal end of a catheter constructed in accordance with an embodiment of the present invention;

FIG. 3 is a schematic view of an arrangement of the layers of a catheter in accordance with the embodiment illustrated in FIG. 2;

FIG. 4 is a cross-sectional view of the catheter of FIG. 2 showing the placement of radiopaque markers around the circumference of the catheter in accordance with one embodiment of the present invention;

FIG. 5 is a perspective view of the distal end of a catheter, showing radiopaque visualization elements constructed in accordance with an embodiment of the present invention;

DETAILED DESCRIPTION

Figure 6:
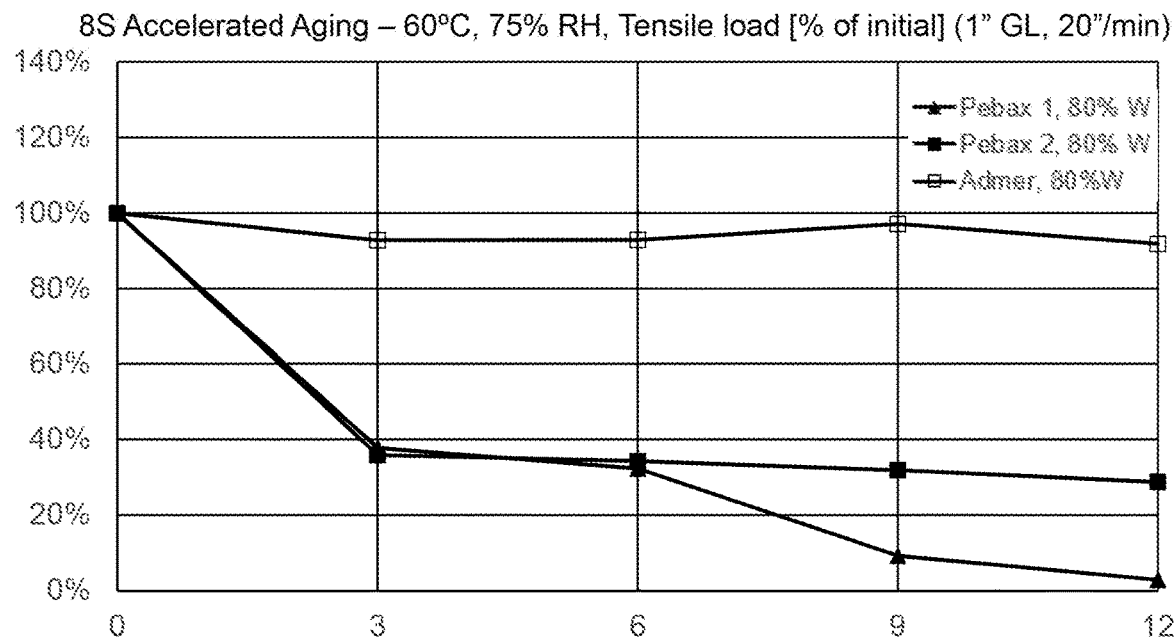
FIG. 6 is a graphical representation of the results of accelerating aging studies on visualization elements, depicting change in tensile load versus equivalent months.

The terms "substantially" or "about" used herein with reference to a quantity includes variations in the recited quantity that are equivalent to the quantity recited, such as an amount that is equivalent to the quantity recited for an intended purpose or function. "Substantially" or derivatives thereof will be understood to mean significantly or in large part.

The term "functionalized" as used herein denotes the condition of adding a functional group to an organic molecule, such as a polymer, in order to alter the chemical properties of the organic molecule. Such chemical properties include, but are not limited to, ionic character, polarity, hydrophobicity/hydrophilicity, and so forth. The term "functional group" is defined as any atom or chemical group that provides a specific behavior.

In one embodiment, a metal in a workable form, such as a powder or a plurality of nanoparticles or microparticles, is compounded into hydrophobic material. The more hydrophobic the material, the better the resistance to cracking or decay due to exposure to moisture, sanitizing fluids, and other environmental sources of hydration. Because catheters and similar medical devices are frequently made of polymers, it may be preferred that the metal powder is dispersed within, surrounded by, or encased in a polymer.

In one embodiment, the hydrophobic material is a polymer. In certain embodiments, the hydrophobic material may be a polymer which has been functionalized to bond nylon. A functionalized polymer is a polymer which contains or has been modified to contain at least one functional group. Various functional groups act to imbue a chemical with certain chemical properties, including but not limited to polarity, ionic charge, hydrophobicity/hydrophilicity, acid/base characteristics, and so forth.

The relative hydrophobicity of the material used in the visualization element may be determined by the amount of water (moisture) absorbed under certain controlled conditions. Absorption is defined as the penetration of moisture into the bulk or body of the material. More hygroscopic (and by extension, less hydrophobic) polymers will draw more moisture into the bulk polymer. This action is driven both by the humidity of the air and the chemical nature, including polarity, of the molecule itself. In general, a polymer is less hydrophobic if it draws more moisture in. The amount of moisture absorbed may be measured, for example, by weight percent.

The quantity of water absorption, from which may be quantified the hydrophobicity of a material, may be measured in a number of ways. In one method, the maximum absorption may be measured by exposure of a polymer composition to 100% relative humidity. In another aspect, the hydrophobicity can be measured according to the requirements of ISO 62, which outlines conditions for testing including exposure of the material to 50% relative humidity at 20 degrees Celsius, and to water at 23 degrees Celsius. Hydrophobicities of different materials can be compared by such a method when the conditions used for absorption measurements are held constant.

Examples of functional groups that may be present or incorporated into a polymer in accordance with an embodiment of the present invention include, but are not limited to, carboxylic acids, acid anhydrides, esters, halides, acyl halides, amides, nitriles, aldehydes, ketones, alcohols, thiols, amines, ethers, alkenes, sulfides, alkynes, alkyl halides, nitro groups, sulfonyl groups, and so forth. A functional group may be present or introduced to any portion of a monomer incorporated into the polymer. In some embodiments, the functional group may be introduced into the polymer by grafting onto, grafting through, or grafting from methodologies. The functional group may be present on all monomer units of the polymer, or the polymer may have a portion of monomer units functionalized, with the remainder not incorporating said functional group. In some cases, at least one monomer subunit of the polymer may include multiple functional groups.

In one embodiment, the polymer of the hydrophobic material may be a polyolefin, such as at least one of a polyethylene, a polypropylene, a polymethylpentene, polybutene-1, polyisobutylene, ethylene propylene rubber, and ethylene propylene diene monomer rubber. Suitable polymers may be linear or branched-chain polymers. In the case of a polyethylene, suitable subtypes of polyethylenes may include low density, medium density, high density, and ultra high molecular weight polyethylenes. The hydrophobic material may include a copolymer, including a block copolymer.

In one embodiment, the functionalized polymer may be functionalized with maleic anhydride. In certain embodiments, the hydrophobic material may include a polyolefin functionalized with maleic anhydride, such as a linear low density polyethylene grafted with maleic anhydride. Such polymers include those that are sold under the trade name ADMER.

In some cases, the medical device in which visualization elements are to be incorporated is made of at least one functionalized hydrophobic polymer plus a second polymer. In some cases, the device may be made of an elastomer, such as a polyether block amide (PEBA). In other embodiments, the device may be made of at least one of a polyester amide, a polyetheresteramide, and a polycarbonate esteramide.

In the case when the device includes a PEBA, it may be preferred to create a material that will more closely match, for example, the mechanical properties of the device body. In such an instance, the base material of the device (PEBA) may be mixed with the functionalized hydrophobic polymer, which will provide resistance to environmental effects and improving shelf life while also providing similar mechanical properties to the remainder of the device. In some embodiments, the polymer character of the visualization element may be 100% functionalized hydrophobic polymer. In another embodiment, the polymer character of the visualization element may be about 3% to about 100% functionalized hydrophobic polymer, with about 97% to about 0%, respectively, the base polymer of the device making up the remainder. The functionalized hydrophobic polymer may make up about 4% to about 90% of the visualization element, or about 5% to about 80%, or about 7.5% to about 75%, or about 10% to about 70%, or about 20% to about 50%, or about 25% to about 40%, or any intervening percentage, with a base polymer from which the device is prinicipally made making up the remainder of the composition.

For a radiopaque metal, tungsten is favored due to its density and cost. Tungsten may be supplied as a powder, or as microparticles or nanoparticles, any of which may be compounded with, dispersed within, or otherwise combined with the functionalized hydrophobic polymer of the visualization element. The tungsten content of a visualization portion may be about 5% to about 30% by volume, or up to about 80% by weight. In some cases, the tungsten content of the visualization element may be about 17% by volume.

It has been found in one embodiment that dispersing a tungsten powder into a 100% polymeric composition of a maleic anhydride-functionalize polyolefin, such as an ADMER, has had the unexpectedly positive result of providing good resistance to environmental factors such as moisture, hydrogen peroxide treatment, and elevated temperature, as well as extending shelf life. Such a finding is described below as Example 1, and in FIGS. 6-7.

FIG. 1 illustrates an embodiment of a polymer/metal layer 10 in which a plurality of radiopaque metal particles 12 are dispersed in a polymer substrate 14. The figure is not necessarily to scale. The radiopaque particles are x-ray reflective, and when incorporated into a medical device, may be viewed by the physician via radiography, fluoroscopy, or other usual visualization techniques. The metal particles 12 may be tungsten in one embodiment, but may also include at least one other metal that has radiopaque characteristics, including but not limited to palladium, iridium, gold, tantalum, bismuth, barium, and platinum. The metal particles 12 may be derived from a powder, or may be nanoparticles or microparticles, or any other form that enables simple handling of the material.

The radiopaque metal particles may be mixed into the polymeric material in an uncoated form. As used herein, a particle is considered "uncoated" if an outer surface of the particle is of a metallic character, or otherwise not encased in, surrounded by, or encompassed by another material, such as a polymer, before dispersion within a layer of polymeric material. The abundant polymer into which a plurality of particles is dispersed will not be considered a coating. Rather, a coating will be considered to be a discrete covering over a nucleus comprising the metal, which will form a coated particle that is then used in the construction of a visualization element. It is an unexpected finding of the study of the present invention that dispersion of uncoated metal particles, particularly tungsten powders, nanoparticles, and microparticles, into a functionalized hydrophobic polymer, both adheres firmly to the base (more hydrophilic) polymer of a medical device body, and is resilient when exposed to higher-temperature, higher-humidity environments compared to other formulations.

A composition for use in making a visualization material in accordance with an embodiment of the present disclosure may be made in a number of different ways. In one case, the functionalized hydrophobic material and the metal powder may be combined using a twin screw extruder, and the resultant material collected and placed into a receiving portion of the pre-made device.

In the construction of a device, at least a portion of the second polymer of the visualization element is in direct contact with the base material of the device body. In some embodiments, the second polymer is chemically, or physicochemically, bonded to the device body, including to the polymer of the device body.

In the case in which a second polymer, such as the base polymer of the device body, is incorporated into the visualization element, the base polymer and the functionalized hydrophobic polymer may be combined first, and then the metal added; or, the metal may first be blended with the functionalized hydrophobic polymer, and then the second (device base) polymer may be blended into the mixture.

The methods of the present disclosure may be particularly useful as they allow for handling of the metal, such as tungsten, in bulk. The method avoids applying a coating to individual particles, and reduces the handling of micron-sized (or smaller) particles to a single bulk step, which simplifies workflow, minimizes loss, and increases efficiency. This arrangement involves direct contact between the metal, such as tungsten, with at least a portion of the functionalized hydrophobic polymer.

In some cases, the device to be made in accordance with the present disclosure may be a catheter, as illustrated in FIG. 2. The catheter 20 has a device body 22, toward the distal end 26 of which a plurality of radiopaque visualization elements 28 are embedded. The catheter 20 also has a lumen 24 running through its length. The radiopaque elements 28 in this case are depicted as linear or rectangular portions which run substantially parallel to a longitudinal axis running through the device, but numerous designs are envisioned beyond this configuration, such as circular or semicircular visualization elements 28 arranged circumferentially around at least a portion of the device body.

One possible configuration of layers at a visualization element of the catheter is depicted in FIG. 3. Base layer 30, made of the first polymeric material 34 which makes up the majority of the device, is an outer layer which makes up an outer surface of the catheter 20. The visualization element layer 32 is, in this embodiment, an inner layer, and contains radiopaque particles 38 dispersed within the polymer layer 36 which includes the functionalized hydrophobic polymer. In this arrangement, the visualization element is exposed in the lumen of the device, and fluid running through the catheter may contact the visualization element. However, other arrangements are possible, including the visualization elements being an outer layer of the catheter, or the visualization elements being positioned between an inner layer and an outer layer of the base material.

FIG. 4 is a cross sectional view of the catheter of FIG. 2. This view shows that the catheter 20 has four visualization elements positioned at substantially equidistant positions around the circumference of the device. It will be appreciated that any number of elements may be used, and as described previously, their arrangement may differ from the linear elements shown.

FIG. 5 is a perspective view of the distal end 126 of a catheter 120 in accordance with the principles of another embodiment of the present invention. In this embodiment, the visualization elements 128 are arranged as circular bands centered around the longitudinal axis of the catheter 120 and embedded in the device body 122. Although three visualization elements 128 are depicted in FIG. 5, any number of such bands may be employed in a device 120.

One possible use for a catheter constructed in accordance with the principles of the present embodiments is for use in a delivery system for a medical implant. Device delivery systems may be used with the Seldinger technique and related percutaneous entry techniques for delivery of implantable medical devices into the vasculature of human or veterinary patients. Such systems may utilize a wire guide inserted into the vasculature to extend to the site of implantation of a medical device such as a stent, stent graft, filter, occluder, valve or the like. An introducer sheath may be placed over a portion of the guide wire, and a catheter inserted over the guide wire within the introducer sheath and beyond its distal tip. The medical device is contained within a distal portion of the catheter until delivery to the site of implantation. The medical device is then released from the catheter distal tip and deployed. The presence of radiopaque elements at the distal end of the catheter assists in delivery by providing information as to where the device will eventually be implanted. Other uses for a catheter constructed in accordance with the principles of the present invention include injection or withdrawal of fluids, or to deliver medications.

Although catheters have been described, it will be appreciated that a number of other medical devices may incorporate visualization portions as described herein. Such devices include, but are not limited to, balloons, balloon catheters, stents, occlusion devices, and intravascular filters.

The following Example illustrates a comparison between visualization members made of two different hydrophilic polymer formulations (20% PEBA by weight) and a functionalized hydrophobic polymer (20% ADMER by weight) visualization element.

EXAMPLE 1

Visualization elements made of a first PEBA (20% by weight), a second PEBA (20% by weight), and a functionalized hydrophobic polymer (ADMER, 20% by weight) were exposed to elevated temperatures (about 60 degrees Celsius) and high humidity (about 75% relative humidity) as part of an accelerated aging program. However, in some instances, humidity as low as 7% relative humidity may be suitable for testing.

All visualization elements included about 80% tungsten by weight. The visualization elements tested were in the form of single lumen extruded tubes made entirely of the visualization material (that is, tungsten compounded into a polymer, in this case either a PEBA or ADMER.) The PEBA tubes have an outer diameter of about 0.0550 inch, and an inner diameter of about 0.0395 inch. The ADMER tubes have an outer diameter of about 0.066 inch and an inner diameter of about 0.045 inch.

Figure 7:
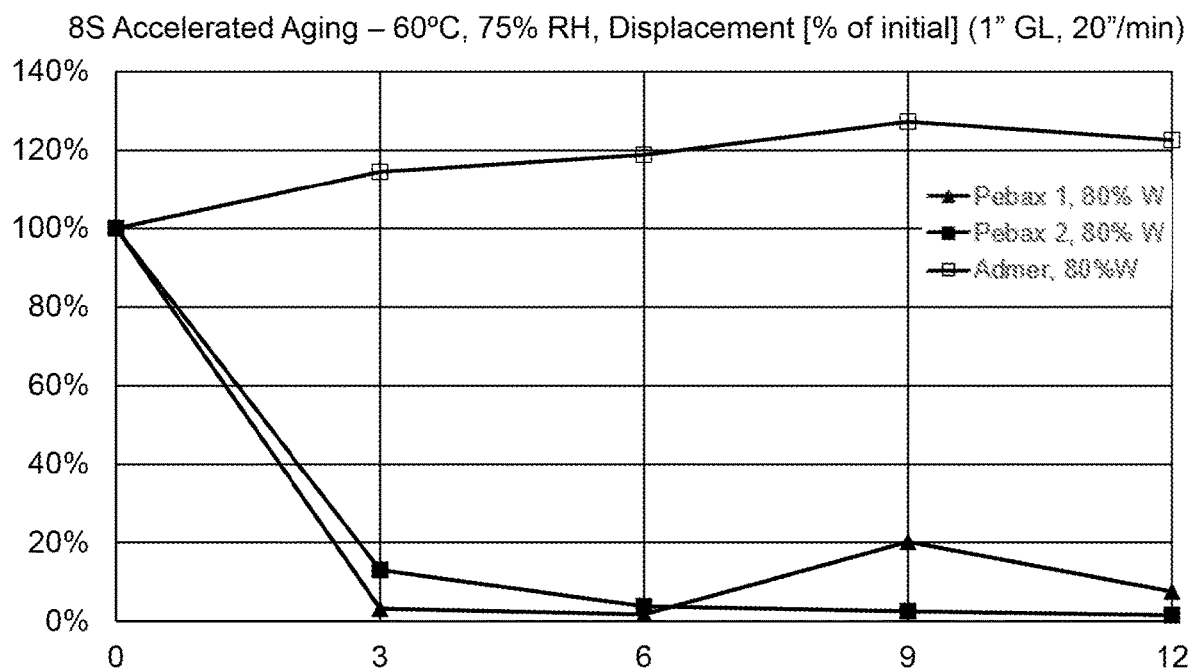
FIG. 7 is a graphical representation of the results of accelerating aging studies on visualization elements, depicting change in displacement versus equivalent months.

The duration of exposure was about 12 accelerated aging equivalent months, with samples being measured at 3 accelerated aging equivalent month increments for both tensile load (in pounds, FIG. 6) and displacement (inches, FIG. 7). An accelerated aging program may be devised by methods known in the medical device industry, making use of an Arrhenius equation-derived calculation as described in, for example, ASTM F1980, which explains that chemical reactions involved in the deterioration of materials follow the Arrhenius reaction rate function. In such a program, the equation governing testing may be $AAF=Q_{10}^{A}(T_{AA}-T_{RT})/10)$, wherein AAF represents the accelerated aging factor, $Q_{10}$ represents an aging factor for a 10° C. increase or decrease in temperature, $T_{AA}$ represents an accelerated aging temperature in degrees Celsius, and $T_{RT}$ is ambient temperature in degrees Celsius. In the presently-used protocol, $Q_{10}=2.0$, and $T_{RT}$ is 22 degrees Celsius, meaning that one day of experimental time is equivalent to about 13.93 days of accelerated aging at a testing temperature of 60° C.

The PEBA visualization elements had an initial relative tensile load that rapidly dropped at the first (three month) time point to less than 40% of the original value and remained low throughout the trial (see FIG. 6). In contrast, and surprisingly, the functionalized hydrophobic polymer visualization element had substantially the same tensile load characteristics after twelve months' equivalent exposure to high heat and high humidity as it did initially (FIG. 6). Similar results were observed for displacement tests (see FIG. 7). Taken together, these trials indicate that the presence of a functionalized hydrophobic polymer, even with tungsten compounded directly therein and in direct contact with said polymer, provides an unexpectedly improved formulation with good resistance to environmental factors such as moisture and elevated temperatures.

As a person skilled in the art will readily appreciate, the above description is meant as an illustration of implementation of the principles this application. This description is not intended to limit the scope of this application in that the system is susceptible to modification, variation and change, without departing from the spirit of this application, as defined in the following claims.

What is claimed is:

1. A medical device comprising: a body portion comprising a first polymeric material, and a visualization portion comprising a second polymeric material more hydrophobic than the first polymeric material, the visualization portion comprising a plurality of particles comprising at least one radiopaque metal, the plurality of particles being in direct contact with and dispersed in the second polymeric material, the visualization portion being in direct contact with an outer surface of the body portion; wherein after twelve months of exposure to 60 degrees Celsius and 75% relative humidity, the visualization portion retains at least 40% of a tensile load of the visualization portion before the twelve months of exposure.

2. The medical device of claim 1, wherein the plurality of particles are uncoated.

3. The medical device of claim 1, wherein the at least one radiopaque metal comprises at least one of tungsten, gold, palladium, iridium, tantalum, bismuth, barium, and platinum.

4. The medical device of claim 3, wherein the at least one radiopaque metal comprises tungsten.

5. The medical device of claim 1, wherein the second polymeric material is a functionalized polymer.

6. The medical device of claim 5, wherein the functionalized polymer comprises a polyolefin.

7. The medical device of claim 5, wherein at least one functional group of the functionalized polymer is maleic anhydride.

8. The medical device of claim 1, wherein the visualization portion further comprises the first polymeric material.

9. The medical device of claim 1, wherein the visualization portion further comprises about 0% to about 97% of the first polymeric material.

10. The medical device of claim 1, wherein the medical device is a catheter comprising a lumen formed therethrough.

11. The medical device of claim 10, wherein the visualization portion is bonded directly to the body portion.

12. The medical device of claim 11, wherein at least a portion of the second polymeric material is bonded directly to at least a portion of the first polymeric material.

13. A method of making the medical device of claim 1, the method comprising:
dispersing a radiopaque material into a functionalized hydrophobic polymer to form a visualization element, the radiopaque material being in direct contact with the functionalized hydrophobic polymer, and
bonding the visualization element to a device body of the medical device.

14. The method of claim 13, wherein the functionalized hydrophobic polymer comprises maleic anhydride.

15. The method of claim 13, wherein the radiopaque material comprises tungsten.

16. The method of claim 15, wherein the tungsten comprises about 5% to about 30% of the visualization element by volume.

17. The method of claim 13, wherein the radiopaque material is provided as one of a powder, a plurality of microparticles, and a plurality of nanoparticles.

18. The method of claim 13, wherein the medical device is a catheter.

19. A medical device, comprising:
a body portion comprising a first polymeric material, and
a visualization portion comprising a second polymeric material more hydrophobic than the first polymeric material, the visualization portion comprising a plurality of particles comprising at least one radiopaque metal, the plurality of particles being in direct contact with and dispersed in the second polymeric material, the second polymeric material being in direct contact with the first polymeric material,
wherein the visualization portion retained the same tensile load and displacement characteristics after three months of exposure to 60 degrees Celsius and 75% relative humidity.

* * * * *